(12) United States Patent
Arnold et al.

(10) Patent No.: US 8,292,923 B1
(45) Date of Patent: Oct. 23, 2012

(54) SYSTEMS AND METHODS FOR TREATING SPINAL STENOSIS

(75) Inventors: Benjamin Arnold, San Diego, CA (US); Jeremy Malik, San Diego, CA (US); Hyun Bae, San Diego, CA (US); Dave Reveley, San Diego, CA (US); Eric Dasso, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 140 days.

(21) Appl. No.: 12/578,577

(22) Filed: Oct. 13, 2009

Related U.S. Application Data

(60) Provisional application No. 61/105,011, filed on Oct. 13, 2008.

(51) Int. Cl.
*A61B 17/70* (2006.01)
(52) U.S. Cl. ...................................... 606/249
(58) Field of Classification Search .................. 606/246, 606/248, 249; 623/17.11
See application file for complete search history.

(56) References Cited

U.S. PATENT DOCUMENTS

| | | | |
|---|---|---|---|
| 5,011,484 A | 4/1991 | Bréard | |
| 5,645,599 A | 7/1997 | Samani | |
| 5,836,948 A | 11/1998 | Zucherman et al. | |
| 6,558,387 B2 | 5/2003 | Errico et al. | |
| 6,695,882 B2 | 2/2004 | Bianchi et al. | |
| 6,699,247 B2 | 3/2004 | Zucherman et al. | |
| 6,723,097 B2 | 4/2004 | Fraser et al. | |
| 6,761,720 B1 | 7/2004 | Senegas | |
| 7,201,775 B2 | 4/2007 | Gorensek et al. | |
| 7,273,498 B2 | 9/2007 | Bianchi et al. | |
| 2001/0020188 A1 | 9/2001 | Sander | |
| 2001/0021850 A1 | 9/2001 | Zucherman et al. | |
| 2003/0040746 A1 | 2/2003 | Mitchell et al. | |
| 2003/0045935 A1 | 3/2003 | Angelucci et al. | |
| 2004/0019356 A1 | 1/2004 | Fraser et al. | |
| 2005/0165398 A1 | 7/2005 | Reiley | |
| 2006/0085070 A1* | 4/2006 | Kim | 623/17.11 |
| 2006/0106381 A1 | 5/2006 | Ferree et al. | |
| 2006/0235532 A1 | 10/2006 | Meunier et al. | |
| 2006/0247634 A1 | 11/2006 | Warner et al. | |
| 2006/0293662 A1* | 12/2006 | Boyer et al. | 606/61 |
| 2007/0032790 A1 | 2/2007 | Aschmann et al. | |
| 2007/0043361 A1 | 2/2007 | Malandain et al. | |
| 2007/0073292 A1* | 3/2007 | Kohm et al. | 606/61 |
| 2007/0093823 A1 | 4/2007 | Booth et al. | |
| 2007/0093825 A1* | 4/2007 | Ferree et al. | 606/61 |
| 2008/0015701 A1* | 1/2008 | Garcia et al. | 623/17.16 |
| 2008/0027438 A1 | 1/2008 | Abdou | |
| 2008/0319549 A1* | 12/2008 | Greenhalgh et al. | 623/17.16 |

\* cited by examiner

*Primary Examiner* — Eduardo C Robert
*Assistant Examiner* — Atiya Mahmud
(74) *Attorney, Agent, or Firm* — NuVasive, Inc.; Jonathan Spangler; Jennifer Russell

(57) ABSTRACT

The present invention involves a system and method for implanting an interspinous spacer configured to self-distract a stenotic interspinous space. The present system includes, but is not necessarily limited to, an interspinous spacer and insertion instrumentation for assisting in the implantation and positioning of the interspinous spacer within an interspinous space.

16 Claims, 9 Drawing Sheets

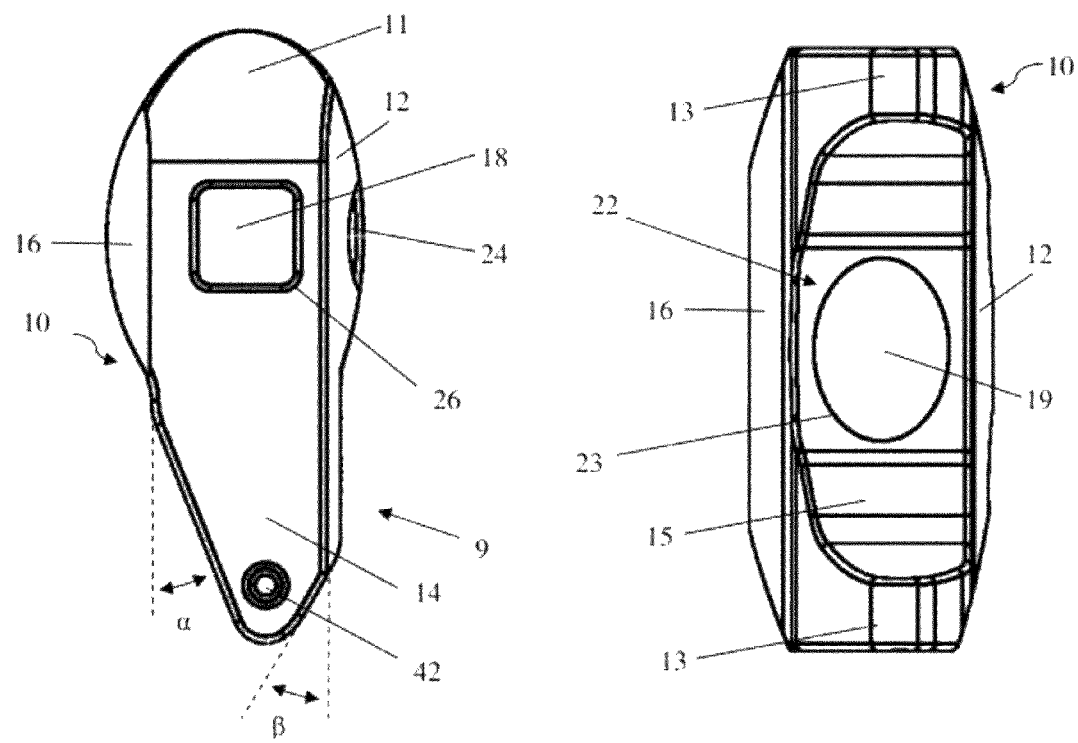
FIG. 5
FIG. 6
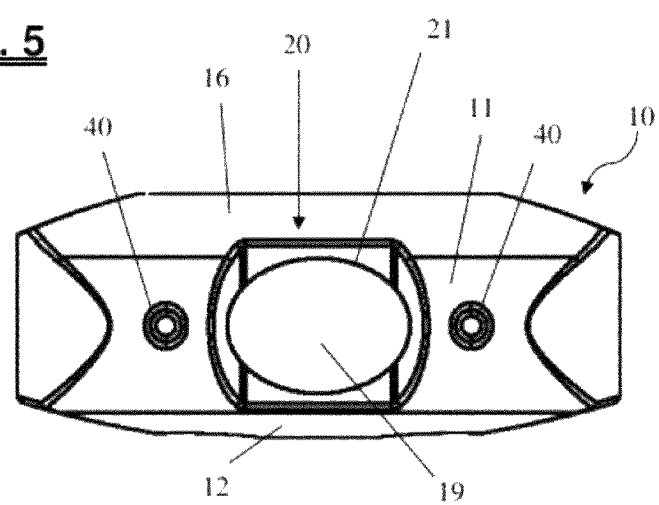
FIG. 7

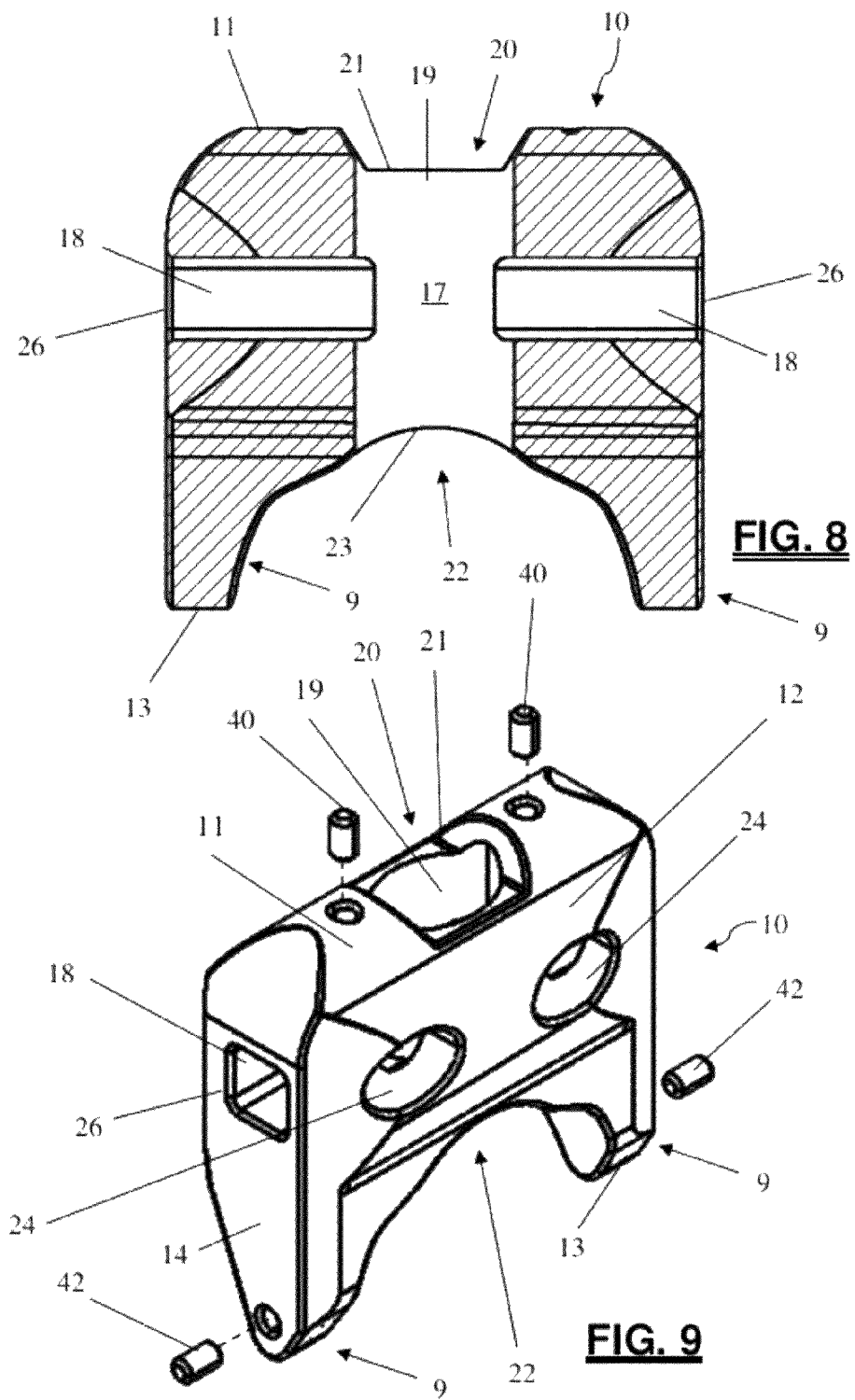

SYSTEMS AND METHODS FOR TREATING SPINAL STENOSIS

CROSS-REFERENCE TO RELATED APPLICATIONS

This application is an non-provisional patent application and claiming the benefit of priority from commonly owned and co-pending U.S. Provisional Patent Application Ser. No. 61/105,011, entitled "Systems and Methods for Treating Spinal Stenosis," and filed on Oct. 13, 2008, the entire contents of which is hereby expressly incorporated by reference into this disclosure as if set forth in its entirety herein.

FIELD

This invention relates generally to spine surgery and, in particular, to methods and apparatus for treating spinal stenosis.

BACKGROUND

Spinal stenosis is a narrowing of spaces in the spine which results in pressure on the spinal cord and/or nerve roots. This disorder usually involves the narrowing of one or more of the following: (1) the canal in the center of the vertebral column through which the spinal cord and nerve roots run, (2) the canals at the base or roots of nerves branching out from the spinal cord, or (3) the openings between vertebrae through which nerves leave the spine and go to other parts of the body. Pressure on the spinal cord and/or exiting nerve roots may give rise to pain or numbness in the legs and/or arms depending on the location within the spine (e.g. cervical, thoracic, lumbar regions). While spinal stenosis generally afflicts those of advanced age, younger patients may suffer as well.

A variety of treatments have been undertaken to alleviate or minimize the effects of spinal stenosis. One such technique is a laminectomy, which involves removing the lamina portion from the pathologic region. By removing the lamina, this procedure enlarges the spinal canal and thus relieves the pressure on the spinal cord and/or compressed nerves. While generally effective, some consider laminectomy disadvantageous in that, as with any procedure involving bone removal, the resulting region of the spine may be further compromised from a mechanical standpoint. Moreover, elderly patients frequently have co-morbidities that increase the likelihood of complications, such as increased back pain, infection, and prolonged recovery.

Still other efforts at treating spinal stenosis involve placing spacer devices within the interspinous space to indirectly decompress the stenotic condition. Typically implanting these spacers requires perforating the supraspinous ligament running along the apices of the spinous processes. The use of one or more additional instruments to distract the interspinous space prior to implanting the spacer is also generally required. The present invention is directed at overcoming, or at least improving upon, the disadvantages of the prior art.

SUMMARY OF THE INVENTION

The present invention is directed at treating spinal stenosis involving an interspinous spacer configured to self-distract a stenotic interspinous space. According to an important aspect of the present invention, the interspinous spacer of the present invention is designed to fuse over time to the spinous processes of the affected spinal level. This is facilitated by abrading the surface of the spinous process where it will mate with the interspinous spacer of the present invention. This junction will fuse over time based, in part, on the fusion-enabling design and/or material of the interspinous spacer of the present invention. The interspinous spacer may also be constructed from non-bone materials (e.g. polyaryletheretherketone (PEEK) and/or polaryletherketoneketone (PEKK)) which are physically designed to promote fusion. This is accomplished, by way of example, by providing an interior lumen within the interspinous spacer which is dimensioned to receive fusion-inducing materials and which is in communication with the abraded surfaces of the given spinous processes. Such fusion promoting materials may include, but are not necessarily limited to BMP (bone morphogenic protein), demineralized bone matrix, allograft cancellous bone, autograft bone, hydroxyapetite, coral and/or other highly porous substances.

The spacer may be used in either an open or minimally invasive spinal fusion procedure. In either type of procedure, a working channel is created in a patient that reaches a targeted spinal level. After the creation of the working channel, the interspinous space is prepared by removing at least a portion of the interspinous ligament and preferably abrading the superior and inferior spinous processes. Abrading the spinous processes includes abrading the inferior portion of the superior spinous process and the superior portion of the inferior spinous process where they will communicate with the fusion promoting materials packed in the main cavity through a superior fusion aperture and inferior fusion aperture. Abrading removes the hard cortical bone from the surface of the bone exposing the softer bleeding cancellous bone underneath which is better adapted for fusion. As new bone generates to heal the abraded portion, the new bone may communicate with the fusion promoting materials and grow into the main cavity of the spacer, thus fixing the spacer to both the superior and inferior spinous processes.

Once the interspinous space has been prepared, a sizer instrument may be used to determine the appropriate size of the spacer required to achieve the desired correction. According to one aspect of the present invention, the implant may be inserted in a horizontal position having an initial height dimensioned to fit within the undistracted interspinous space and then rotated to a vertical position thereby distracting the interspinous space to the desired height. To accomplish this, the surgeon will use an insertion instrument to guide the spacer in between the spinous processes, leading with the bottom surface and guiding the bottom surface around the supraspinous ligament. The spacer is then axially rotated so the top side of spacer faces the posterior side of the spine and the lateral sides of the implant are positioned on either side of the supraspinous ligament. Spacer is then rotated to its final vertical position allowing the spacer to distract the spine at the spinal processes and prevent over extension.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 5 is a side view of the interspinous spacer according to the embodiment shown in FIG. 1;

FIG. 6 is a bottom view of the interspinous spacer according to the embodiment shown in FIG. 1;

FIG. 7 is a top view of the interspinous spacer according to the embodiment shown in FIG. 1;

FIG. 8 is a cross-sectional view of the interspinous spacer according to the embodiment shown in FIG. 1;

FIG. 9 is a perspective view of the interspinous spacer according to the embodiment shown in FIG. 1 with markers exploded;

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The spinal implant system disclosed herein boasts a variety of inventive features and components that warrant patent protection, both individually and in combination.

Figure 1:
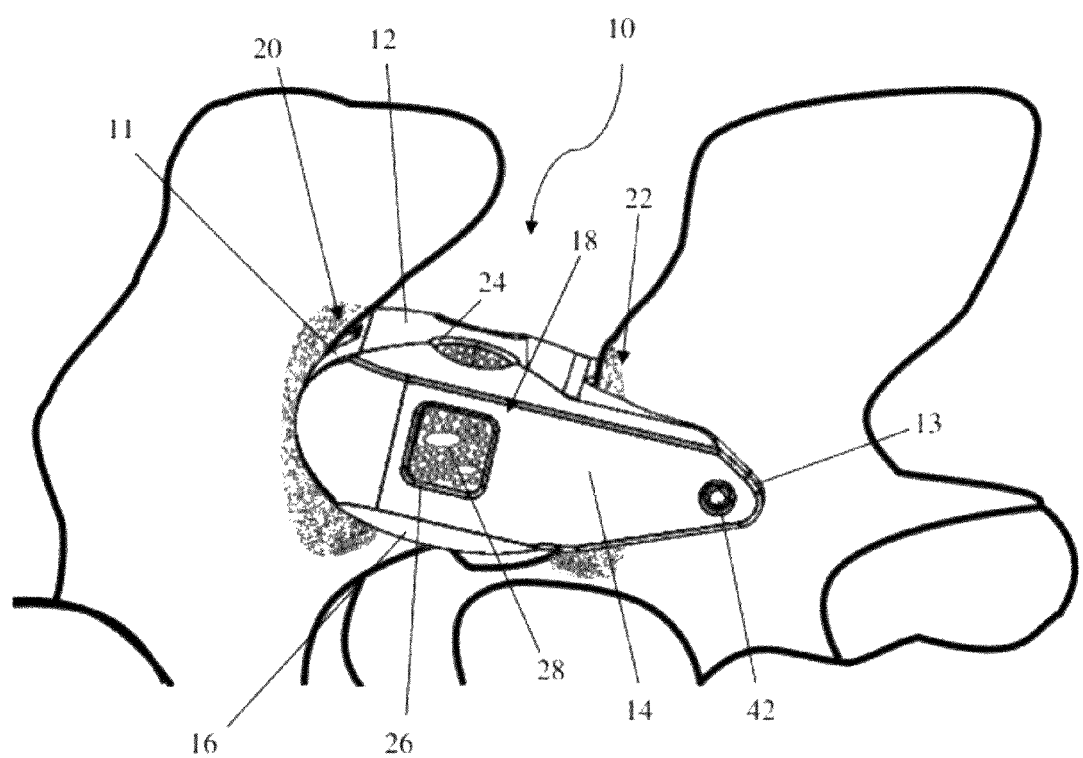
FIG. 1 is a perspective view of an interspinous spacer according to one example embodiment and in use and affixed between a superior spinous process and an inferior spinous process of a human spine.

FIG. 1 illustrates a perspective view of a spinous process spacer 10 of the present invention in use between two spinous processes in a human spine. Spacer 10 includes a top surface 11, posterior side 12, bottom surface 13, lateral sides 14, and anterior side 16. Top surface 11 may further include superior fusion notch 20, and bottom surface 13 may further include inferior fusion notch 22. Spacer 10 may be further provided with a plurality of fusion apertures including, but not limited to, superior fusion aperture 21, inferior fusion aperture 23 and posterior fusion apertures 24 all linked to a main cavity 17. Insertion apertures 26 may be provided on lateral sides 14. As will be described in greater detail below, spacer 10 may preferably be coupled to both a superior and inferior spinal process. This may be accomplished, by way of example only, by snugly positioning spacer 10 between both spinous processes and allowing boney ingrowths to form between the superior and inferior spinous processes through spacer 10.

In a preferred embodiment, spacer 10 is constructed of non-bone material. Suitable non-bone materials may include, but are not necessarily limited to, polyaryletherketone, polyetheretherketon (PEEK) and polyaryletherketoneketone (PEKK). Numerous advantages may be gained by constructing spacer 10 out of materials such as PEEK and PEKK. One advantage is the stiffness properties of PEEK and PEKK closely match that of bone which substantially reduces the likelihood that the spinous process will remodel around spacer 10 causing a re-narrowing of the foraminal height and potentially resulting in the potential need for revision surgery. PEEK and PEKK are also substantially radiolucent which allows for improved post operative visualization of fusion between the superior and inferior spinous processes through spacer 10.

Spacer 10 is designed to maintain the interspinous space between the spinous processes and prevent over extension while boney fusion takes place between the spinous process over time. The fusion process may be augmented by disposing any number of suitable fusion-inducing materials 28 within the main cavity 17, including but not limited to BMP (bone morphogenic protein) 1, 2, 3, 4, 5, 6, 7, 8, 9, 10, 11, 12, 13, 14 . . . n, demineralized bone matrix, allograft cancellous bone, autograft bone, hydroxyapetite, coral and/or other highly porous substance. The fusion inducing material 28 may be packed within main cavity 17 to thereby communicate openly with the superior and inferior spinous processes through any of the insertion instrument apertures 26 and/or fusion apertures 21, 23 and 24. Through this communication, fusion may occur between the superior and inferior spinous processes through the main cavity 17, fixing spacer 10 in position. The cross section of the main cavity 17 is shaped and dimensioned to allow for a sufficient amount of bone growth to form through the cavity, thus fusing and securing the spacer 10 in the interspinous process space. By way of example, the main cavity 17 is shown as being elliptical in shape with a length dimension of approximately 5 mm and a height dimension ranging from approximately 3 mm and 5 mm. Although the main cavity 17 is shown and described as being elliptical in shape with the aforementioned dimensions, the main cavity 17 may be any shape and dimensions appropriate to allow secure bone fusion of the spacer 10 to the surrounding spinous processes without departing from the scope of the present invention.

Figure 2:
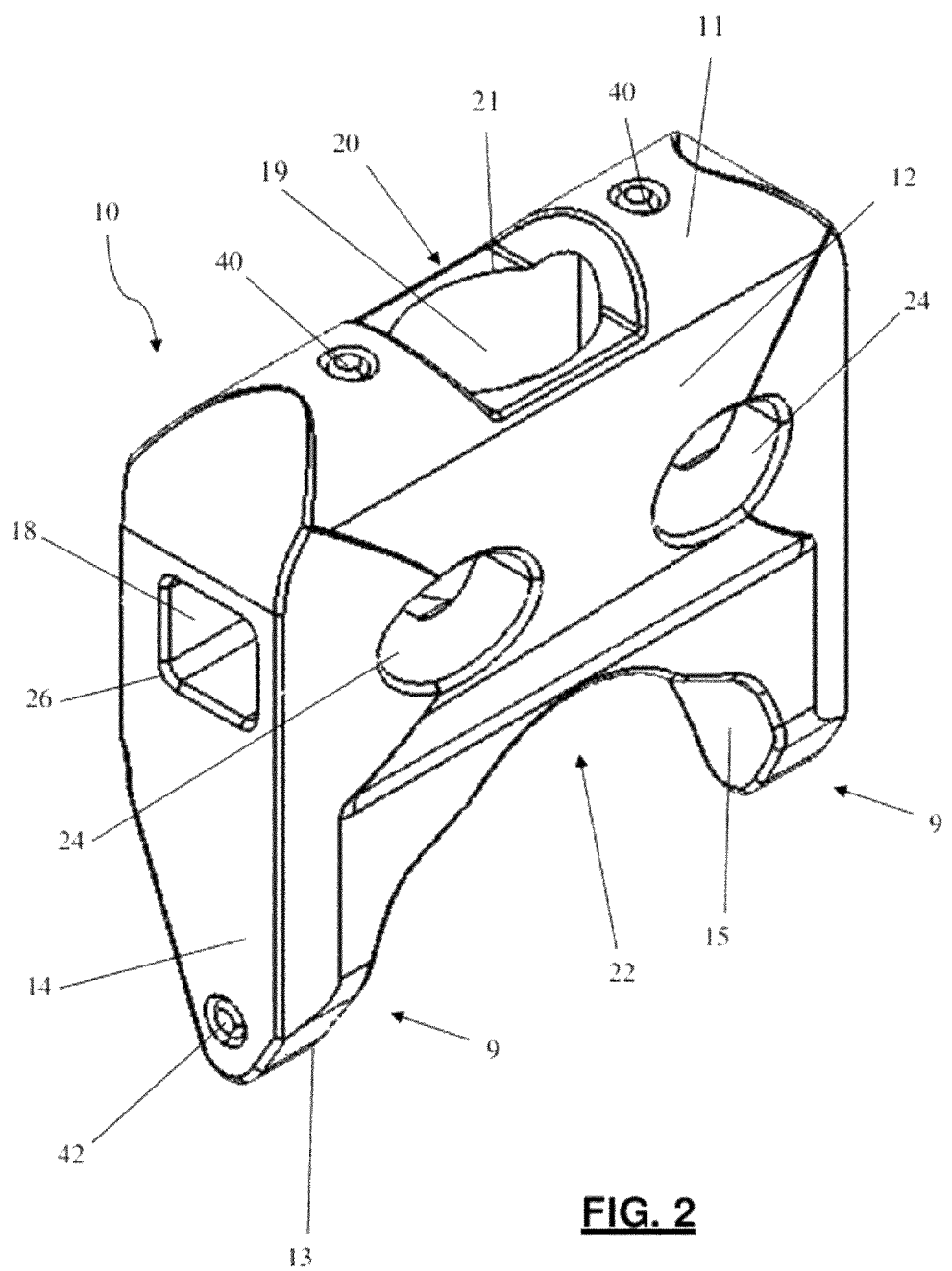
FIG. 2 is a perspective view of the interspinous spacer according to the embodiment shown in FIG. 1.
Figure 3:
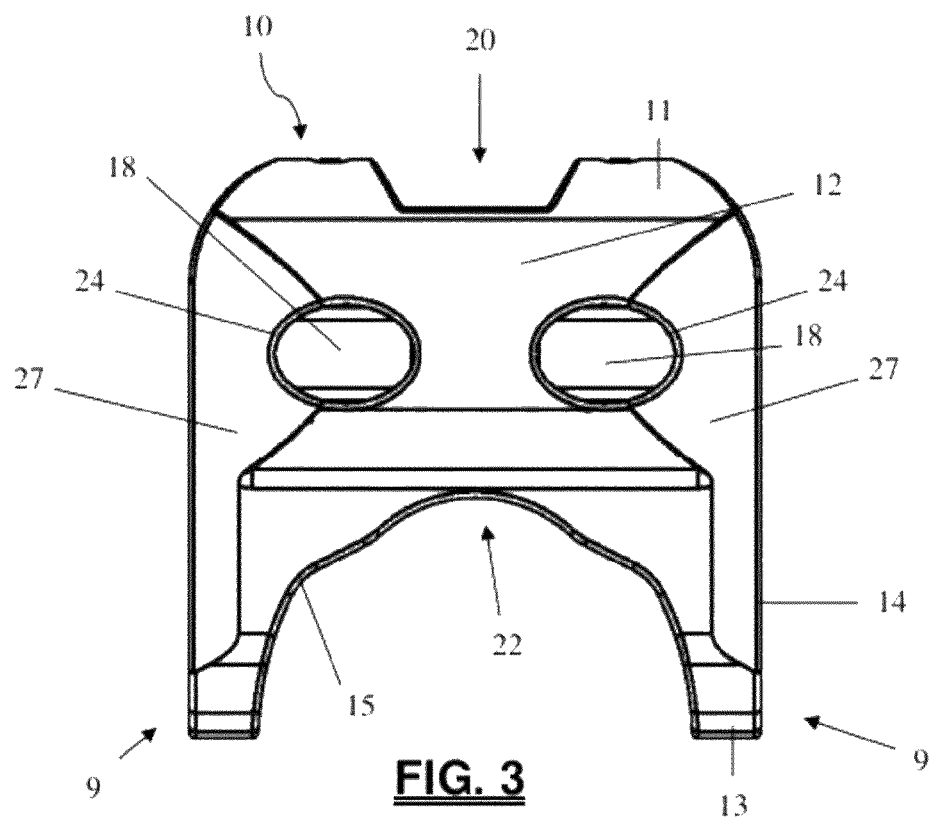
FIG. 3 is a posterior view of the interspinous spacer according to the embodiment shown in FIG. 1.

Spacer 10 and various features thereof are described according to one example, as illustrated in FIGS. 2-8. FIG. 2 is a perspective view of the spacer 10. FIG. 3 is an illustration of posterior side 12 of spacer 10. Superior fusion notch 20 may be located generally on the top surface 11 and centrally positioned between the two lateral sides 14. Fusion notch 20 generally comprises of a slot or indent dimensioned to receive an inferior portion of a superior spinous process. Fusion notch 20 may help center spacer 10 relative to the superior spinous process and may assist in limiting lateral motion of spacer 10 prior to fusion. Fusion notch 20 includes superior fusion aperture 21 (best viewed in FIG. 7) which extends into main cavity 17 and is the primary passage for fusion between main cavity 17 and the superior spinous process. One or more fusion apertures 24 may also be provided on posterior side 24. Posterior fusion apertures 24 may provide an additional avenue for boney growth around the exterior of spacer 10 and may also be used to pack main cavity 17 with fusion promoting materials before and/or after insertion of spacer 10.

The spacer 10 is shaped such that the greatest height between the top and bottom surface 11, 13 of the spacer 10 exist along the lateral sides 14, forming legs 9 extending below a central body portion. The legs 9 of the spacer 10 are increasingly tapered as they converge towards the bottom surface 13 (best shown in FIG. 5 and FIG. 8). The anterior side 16 of the legs 9 taper towards the posterior side 12 of the legs 9, having a taper angle α (FIG. 5). By way of example only, angle α may be approximately 15 to 30 degrees. The posterior sides 12 of the legs 9 begin to taper towards the anterior sides 16 of the legs 9 near the bottom surface 13, having a taper angle β (FIG. 5). By way of example only, angle β may be approximately 20 to 40 degrees. The bottom surface 13 provides a rounded transition between the anterior and posterior sides 16, 12 of the legs 9. Tapering of the legs 9 also occurs in the lateral direction due to the increasing radii of the inferior fusion notch and the medial surface, as will be discussed in more detail below. By way of example, the taper of legs 9 facilitate insertion and through and around tissue (e.g. supra spinous ligament) and distraction of the interspinous space during insertion.

An inferior fusion notch 22 is located generally along the inferior surface of the spacer and is generally positioned centrally between the lateral sides 14. Inferior fusion notch 22 is generally comprised of an angled concave surface dimensioned to receive a superior portion of an inferior spinous process. Fusion notch 22 also helps center spacer 10 relative to the inferior spinous process and may assist in limiting lateral motion of spacer 10 prior to fusion. Inferior fusion notch 22 includes an inferior fusion aperture 23 which extends into main cavity 17 and is the primary passage for fusion between main cavity 17 and the inferior spinous process. FIG. 3 illustrates the medial surface 15 having a generally concave configuration from the bottom surface of legs 9 to the inferior fusion notch 22. By way of example only, the concave inferior fusion notch 22 may have a radius dimension of approximately 5 mm to 8 mm and the concave medial surfaces 15 may have a radius dimension of approximately 10 mm to 15 mm. The more narrow fusion notch 22 generally assists in maintaining the final positioning of the spacer 10 until fusion occurs while the broader arc of the medial surfaces 15 aid in the insertion of the spacer 10 within an interspinous process space, as described below.

Fusion apertures 21, 23 and 24 may be provided in any of a variety of shapes in addition to the generally oval shapes shown, including but not necessarily limited to, generally square, rectangular, circular, triangular and/or any combination thereof. Insertion instrument apertures 18 are positioned along the lateral sides 14 to facilitate introduction of the spacer into a desired position. For example, the spacer may be introduced without sacrificing the supraspinous ligament. In a preferred embodiment, the insertion instrument aperture 18 is a non-circular shape. The non-circular shape of the insertion instrument aperture 18 restricts the relative rotation between the insertion instrument and the spacer while rotating the spacer 10 to the desired interspinous position during introduction. By way of example only, the insertion apertures 18 may have a square profile with height and width dimensions generally in the range of 3 mm to 5 mm. However, the shape and dimensions of the insertion apertures 18 may be any shape and dimension appropriate to permit the desired insertion and rotation of the spacer 10.

Figure 4:
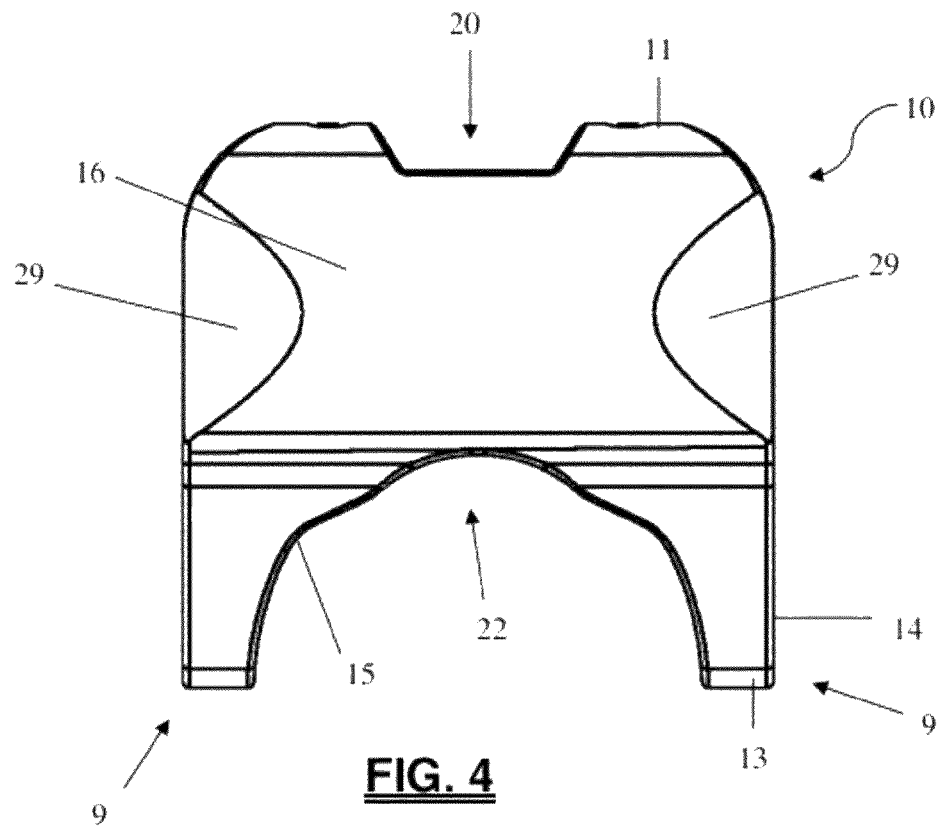
FIG. 4 is an anterior view of the interspinous spacer according to the embodiment shown in FIG. 1.

FIG. 4 is an illustration of anterior side 16 of spacer 10. The anterior surface is generally curved to accommodate a smooth transition during insertion and rotation of the spacer 10 into the desired position within the interspinous space. When positioned in the inter spinous space, the anterior side 16 faces the spinal canal. Preferably, there are no fusion apertures along the anterior side 16 of the spacer 10, which protects the dura and prevents graft material from falling into the dura from within the spacer 10. Both posterior side 12 and anterior side 16 have angled surfaces 27 and 29, respectively, near lateral sides 14 to further accommodate the installation process as described below. For example, angled surfaces 27 and 29 ensure that there are no sharp edges that can damage any surrounding bone or tissue during implantation of the spacer 10. The angled surfaces 27 and 29 also assist in clearance of the lamina and facet joints during introduction and positioning of the implant.

Both the anterior and posterior surfaces of the spacer 10 are generally convex to provide for a smooth transition during insertion and rotation of the spacer 10 into a desired position within the interspinous space. Preferably, the greatest distance between the convex anterior and posterior surfaces is less than the shortest distance between the inferior and superior fusion notches 22, 20. This allows the spacer 10 to distract the spinous processes upon rotation from between an initial insertion position and a final position. The spacer is inserted in a horizontal position and then rotated into a vertical position, as will be discussed in greater detail below. According to one example, and by way of example only, 2 mm to 6 mm of distraction can be effected upon rotation of the spacer 10 within the interspinous process space. However, more or less distraction can be accomplished using the spacer 10 without departing from the scope of the present invention.

FIG. 5 is an illustration of a lateral side 14 of spacer 10. Insertion apertures 26 may be provided on lateral sides 14 and preferably connect into main cavity. Apertures 26 are provided on both lateral sides 14 such that spacer 10 may be inserted from either side of the patient. Apertures 26 are dimensioned to receive insertion head 34 of insertion instrument 30 as described below. FIG. 6 is a bottom view of spacer 10. FIG. 7 is a top view of spacer 10. Top surface 11 of spacer 10 is generally curved and tapers at an angle to the lateral sides 14.

As depicted in FIGS. 5-8, main cavity 17 may preferably be formed from horizontal cavity 18 and vertical cavity 19. Horizontal cavity 18 preferably spans across insertion apertures 26. Horizontal cavity 18 may be provided in any variety of shapes in addition to the generally square shape shown, including but not necessarily limited to, generally rectangular, circular, oblong, triangular and/or any combination thereof. Vertical cavity 19 preferably spans across fusion apertures 21 and 23. Vertical cavity 19 may be provided in any variety of shapes in addition to the generally oblong shape shown, including but not necessarily limited to, generally rectangular, circular, oblong, triangular and/or any combination thereof. In a cross-sectional view, the main cavity 17 has a generally cross-shaped pattern.

To assist in visualization of spacer 10, both during and after surgery, spacer 10 may include at least one marker. FIG. 9 shows in exploded view, by example only, four markers situated within spacer 10. Preferably, spacer 10 includes two top markers 40 and two side marker 42. Markers 40 and 42 may be comprised of biocompatible radiopaque material, such as, for example only, titanium (or other metals or polymers). Markers 40 may be positioned along top surface 11 of spacer 10 on either side of fusion notch 20. Markers 42 may be located in lateral sides 14 below main cavity 17 and preferably adjacent to bottom surface 13. During and after placement of the spacer 10, markers 40 and 42 may be viewable using X-ray fluoroscopy to ensure spacer 10 is correctly oriented in the interspinous space.

Figure 10:
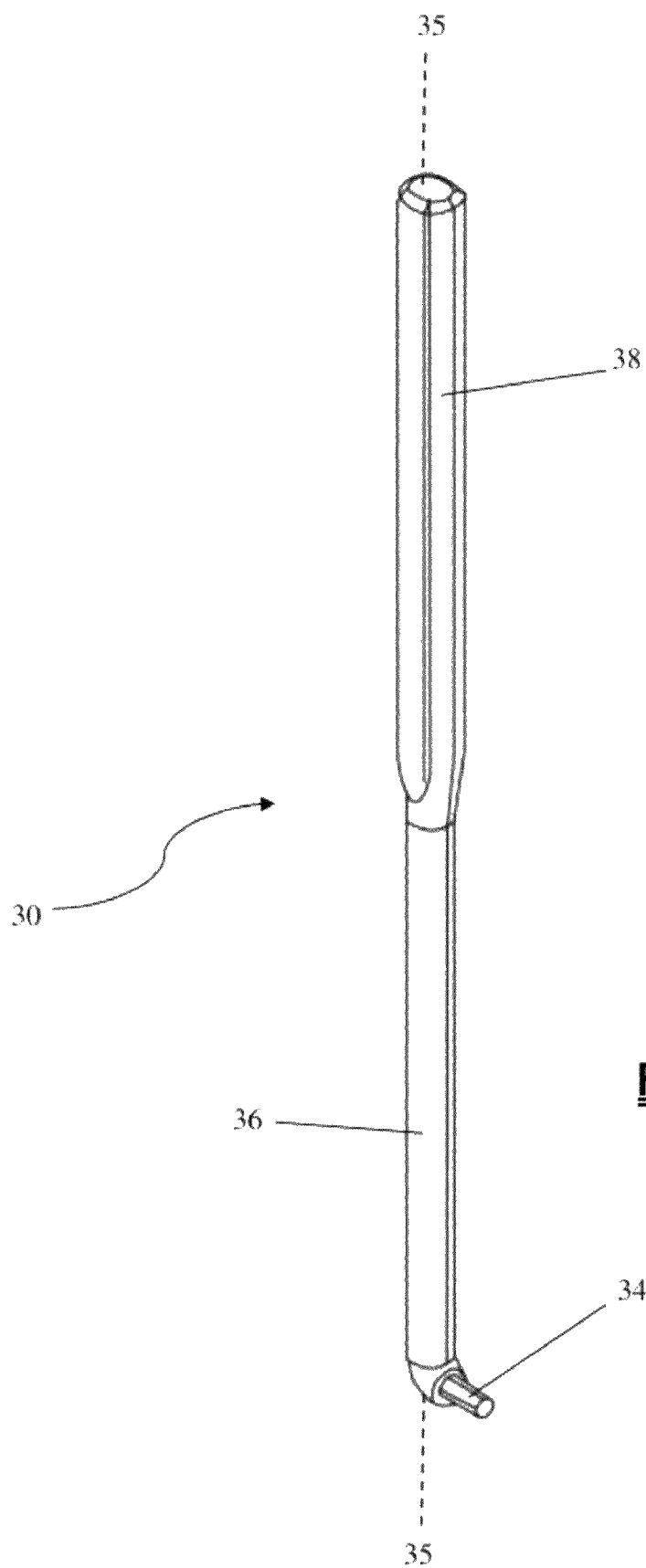
FIG. 10 is a perspective view of an insertion instrument according to one example embodiment used to install the interspinous spacer of FIG. 1.
Figure 11:
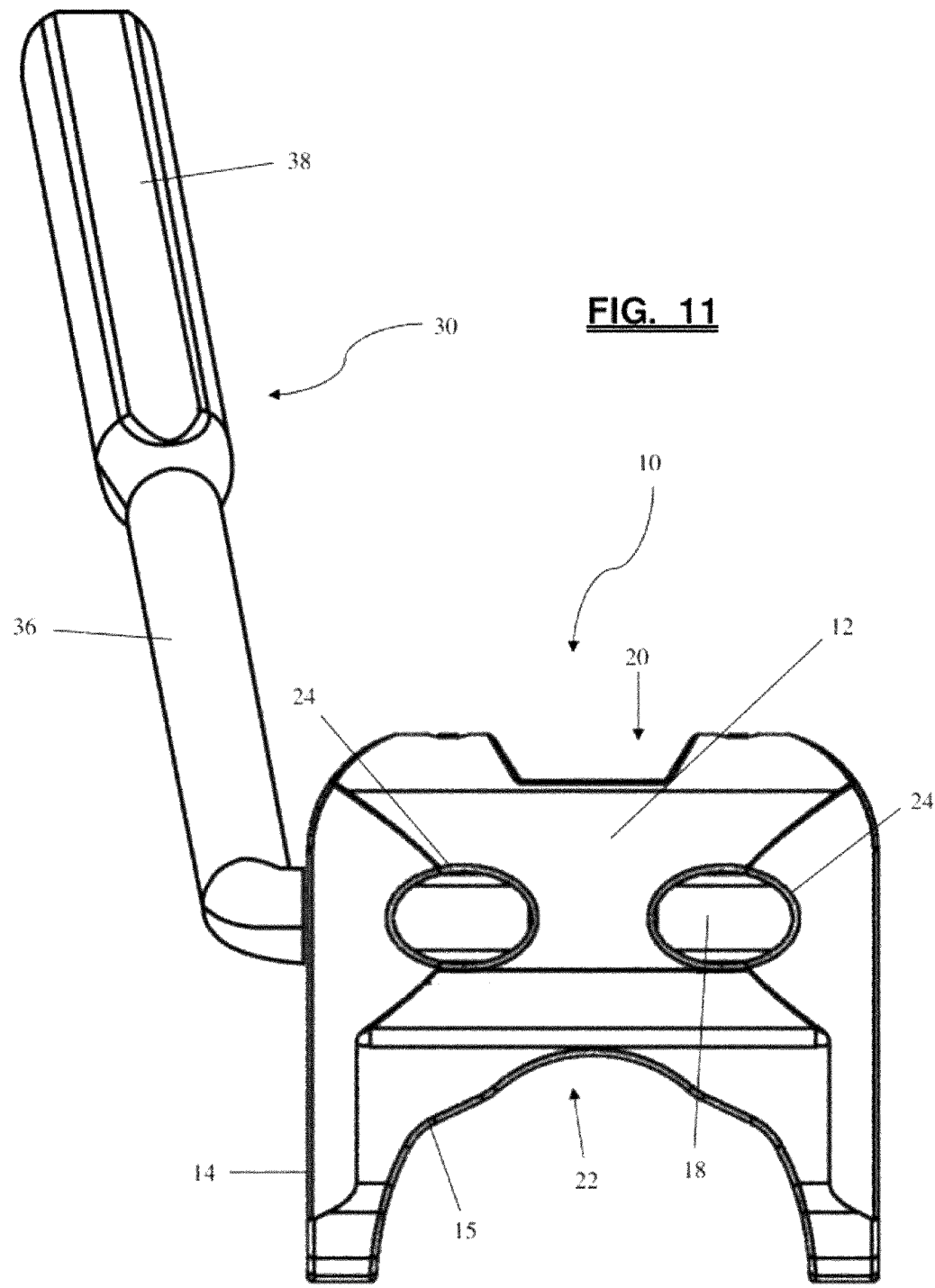
FIG. 11 is a posterior view of the insertion instrument attached to the interspinous spacer of FIG. 1 in preparation for introduction to a target site.

FIG. 10 shows an example embodiment of an insertion instrument 30. Insertion instrument 30 consists of insertion head 34 connected by an elongated body 36 to handgrip 38. Insertion head 34 is oriented at a non-straight angle relative to the longitudinal axis 35 of the instrument 30. The insertion head 34 is configured and shaped to be received by either insertion aperture 26 of the spacer 10. The cross-sectional geometry of the insertion head 34 may be shaped in any of a variety of shapes in addition to the generally square shape shown, including, but not necessarily limited to, generally rectangular, oblong, triangular and/or any combination thereof, such that insertion head 34 matches the shape of the insertion aperture 26. The insertion head 34 may include a slight increasing taper from the tip of head 34 to the body 36. The tapered head 34 interacts with the insertion aperture 26 on the implant 10 to cause a friction fit connection and releasably maintain the spacer 10 on the insertion instrument 30 during the implantation process. FIG. 11 shows insertion instrument 30 inserted into spacer 10 via insertion aperture 26. It will be appreciated that the insertion instrument 30 may be connected to an insertion aperture 26 located on either side of the spacer 10. Preferably, spacer 10 may be positioned on the insertion head 34 such that the vertical orientation of the spacer 10 forms a non-right angle with the longitudinal axis of the instrument 30. This angular offset between the spacer 10 and the instrument 30 may facilitate the rotation of the spacer from the first insertion position to the second distraction position, which will be described in more detail below.

A clinician can utilize the spacer 10 in either an open or minimally invasive spinal fusion procedure. In either type of procedure, a working channel is created in a patient that reaches a targeted spinal level. After the creation of the working channel, the interspinous space is prepared. The interspinous space is prepared by removing at least a portion of the interspinous ligament and preferably abrading the superior and inferior spinous processes. Abrading the spinous processes includes abrading the inferior portion of the superior spinous process and the superior portion of the inferior spinous process. This allows the abraded surfaces to communicate with the fusion promoting materials packed in the main cavity 17 through a superior fusion aperture and inferior fusion aperture of the spacer 10. Abrading removes the hard cortical bone from the surface of the bone and exposes the softer bleeding cancellous bone underneath, which is better adapted for fusion. As new bone generates to heal the abraded portion, the new bone may communicate with the fusion promoting materials and grow into the main cavity 17 of the spacer 10, thus fixing the spacer 10 to both the superior and inferior spinous processes.

Figure 12:
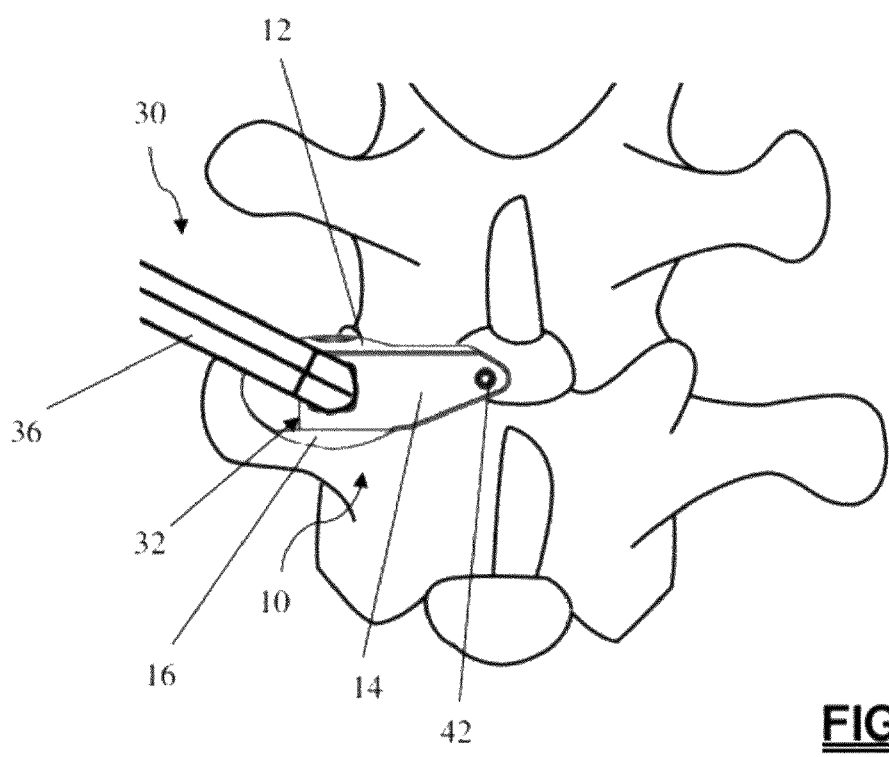
FIGS. 12-14 illustrate in progressive fashion the insertion of the spacer in a first orientation having a diminished height and then the rotating of the spacer to effect distraction of the interspinous space, according to one example embodiment of the present invention.
Figure 13:
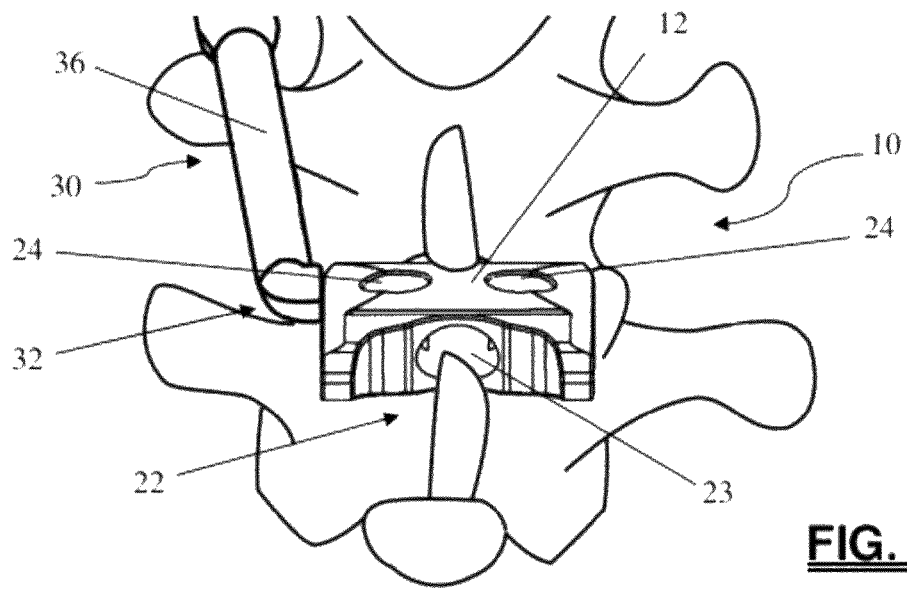
Figure 14:
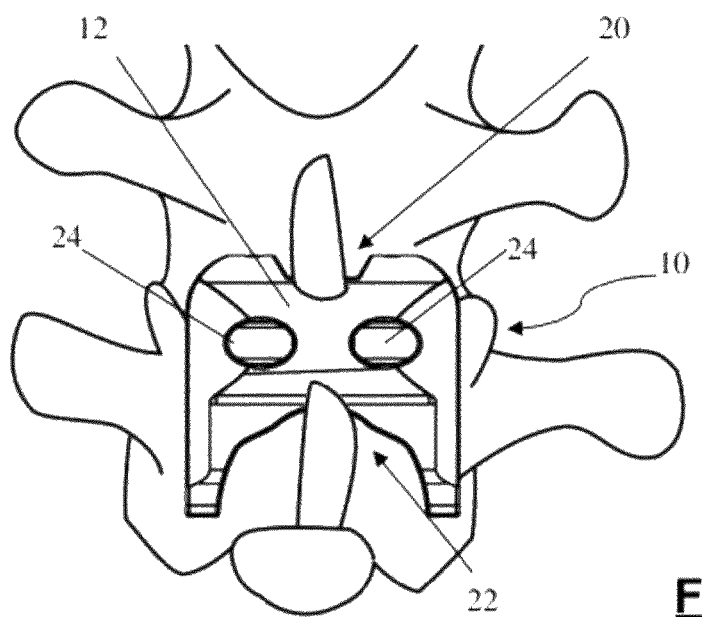

Once the interspinous space has been prepared, a sizer instrument may be used to determine the appropriate size of the spacer required to achieve the desired correction. According to one aspect of the present invention and illustrated in FIGS. 12-14, the spacer may be inserted in a horizontal position having an initial height less than the desired corrected height of the interspinous space and then rotated to a final vertical position thereby distracting the interspinous space to the desired height. To accomplish this, the surgeon will use an insertion instrument 30 to guide the spacer 10 in between the spinous processes, leading with the bottom surface 13 and guiding one of the legs 9 around the supraspinous ligament. The tapered end of leg 9 aids in passing the leg under the supraspinous ligament and can also distract the spinous processes if necessary. Once the first leg 9 is passed under the supra spinous process, the spacer 10 may be axially rotated in the transverse plane to an intermediate position. To get to the intermediate position, the spacer may be rotated approximately 90 degrees such that the top surface 11 faces the spinal canal. From the intermediate position, the spacer 10 may be adjusted into the final position by rotating the spacer again, this time in the sagittal plane. The spacer may be rotated approximately 90 degrees such that the top surface faces the superior spinous process above. As the spacer is rotated into the final position the height of the implant distracts the spinal processes and prevents over extension. X-Ray fluoroscopy or other suitable imaging techniques may be used to verify the spacer 10 is properly positioned. The instrument 30 is removed from the spacer 10 and the working channel is closed.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. A spacer for positioning in an inter-spinous space between a superior spinous process and an inferior spinous process, comprising:
a body composed of non-bone, radiolucent material having opposing anterior and posterior surfaces, opposing first and second lateral surfaces, and opposing top and bottom surfaces, wherein said top surface includes at least one superior fusion notch for receiving at least a part of said superior spinous process when said implant is positioned in said inter-spinous space, said bottom surface including at least one inferior fusion notch for receiving at least a part of said inferior spinous process when said implant is positioned in said inter-spinous space, said lateral sides and said inferior notch defining a pair of legs separating a central body portion having a height less that said legs, said legs including tapered ends, said top surface and said bottom surface further including at least one aperture that extends into said spacer, said first and second lateral surfaces having at least one attachment aperture for releasably coupling said spacer to an insertion tool for inserting said spacer in a posterior surgical approach, said posterior surface having at least one aperture that extends into said spacer, said apertures of said spacer all linking to a main cavity within said spacer, said main cavity generally extending between said top surface and said bottom surface for allowing boney ingrowth to form between said superior and said inferior spinous processes, said anterior surface being a solid surface without any apertures, and at least one image enhancing element is disposed within said spacer to facilitate proper positioning of said spacer between said superior and inferior spinal processes.

2. The inter-spinous process spacer of claim 1, wherein said spacer is composed of a polymer composition.

3. The inter-spinous process spacer of claim 1, wherein said superior fusion notch along said top surface is centrally located between said lateral sides.

4. The inter-spinous process spacer of claim 1, wherein said inferior fusion notch along said bottom surface is centrally located between said lateral sides.

5. The inter-spinous process spacer of claim 3, wherein said superior fusion notch includes a superior fusion aperture extending into said spacer and linking to form at least a part of said main cavity.

6. The inter-spinous process spacer of claim 4, wherein said inferior fusion notch includes an inferior fusion aperture extending into said spacer and linking to form at least a part of said main cavity.

7. The inter-spinous process spacer of claim 1, wherein said at least one image enhancing element includes a radiopaque marker.

8. The inter-spinous process spacer of claim 7, wherein a first radiopaque marker is disposed on said first lateral surface, a second radiopaque marker is disposed on said second lateral surface, and third and fourth radiopaque markers are disposed on said top surface.

9. The inter-spinous process spacer of claim 8, wherein said first and second radiopaque markers are further positioned below said main cavity adjacent said bottom surface and along said first and second lateral sides, respectively.

10. The inter-spinous process spacer of claim 1, further comprising an osteoinductive material positioned at least within one of said apertures and adjacent to said spacer before and/or after insertion of said spacer in said inter-spinous space.

11. The inter-spinous process spacer of claim 10, wherein said osteoinductive material includes at least one of a bone morphogenic protein, demineralized bone matrix, allograft cancellous bone, autograft bone, hydroxyl appetite, coral and other highly porous substance.

12. The inter-spinous process spacer of claim 1, wherein the distance between said lateral sides is generally between 20 mm and 35 mm.

13. The inter-spinous process spacer of claim 1, wherein the distance between said top and bottom surfaces along the lateral sides is generally between 20 mm and 35 mm.

14. The inter-spinous process spacer of claim 1, wherein the distance between said superior and inferior fusion notch is generally between 8 mm and 20 mm.

15. The inter-spinous process spacer of claim 1, wherein rotation of the spacer from a generally horizontal position to a generally vertical position between said superior and inferior spinous process is able to self distract the inter-spinous space approximately between 2 mm to 6 mM.

16. A method for inserting a spacer into an interspinous space between a pair of spinous processes, comprising the steps of:

a. abrading a portion of the pair of spinous processes;
b. positioning at least a portion of said spacer between said spinous processes in a first position; said spacer comprising a body composed of non-bone, radiolucent material having opposing anterior and posterior surfaces, opposing first and second lateral surfaces, and opposing top and bottom surfaces, wherein said top surface includes at least one superior fusion notch for receiving at least a part of said superior spinous process when said implant is positioned in said inter-spinous space, said bottom surface including at least one inferior fusion notch for receiving at least a part of said inferior spinous process when said implant is positioned in said inter-spinous space, said lateral sides and said inferior notch defining a pair of legs separating a central body portion having a height less that said legs, said legs including tapered ends, said top surface and said bottom surface further including at least one aperture that extends into said spacer, said first and second lateral surfaces having at least one attachment aperture for releasably coupling said spacer to an insertion tool for inserting said spacer in a posterior surgical approach, said posterior surface having at least one aperture that extends into said spacer, said apertures of said spacer all linking to a main cavity within said spacer, said main cavity generally extending between said top surface and said bottom surface for allowing boney in-growth to form between said superior and said inferior spinous processes, said anterior surface being a solid surface without any apertures, and at least one image enhancing element is disposed within said spacer to facilitate proper positioning of said spacer between said superior and inferior spinal processes
c. rotating said spacer approximately 90 degrees in a first plane;
d. rotating said spacer approximately 90 degrees in a different plane to seat said spacer in a final position.

* * * * *